United States Patent
Mou et al.

(10) Patent No.: US 11,460,022 B2
(45) Date of Patent: *Oct. 4, 2022

(54) DEVICE HAVING ACTUATING AND SENSING MODULE

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Hsuan-Kai Chen, Hsinchu (TW); Wei-Ming Lee, Hsinchu (TW); Chang-Yen Tsai, Hsinchu (TW)

(73) Assignee: MICROJET TECHNOLOGY CO., LTD., Hsinchu (TW)

(*) Notice: Subject to any disclaimer, the term of this patent is extended or adjusted under 35 U.S.C. 154(b) by 774 days.

This patent is subject to a terminal disclaimer.

(21) Appl. No.: 16/056,789

(22) Filed: Aug. 7, 2018

(65) Prior Publication Data
US 2019/0056292 A1    Feb. 21, 2019

(30) Foreign Application Priority Data
Aug. 21, 2017   (TW) .................................. 106128273

(51) Int. Cl.
*F04B 45/047* (2006.01)
*G01N 1/10* (2006.01)
(Continued)

(52) U.S. Cl.
CPC ............ *F04B 45/047* (2013.01); *F04B 53/20* (2013.01); *G01N 1/10* (2013.01); *G01N 1/2273* (2013.01);
(Continued)

(58) Field of Classification Search
CPC ........ F04B 39/16; F04B 53/20; F04B 45/047; G01N 1/2273; G01N 1/10; G01N 33/0062;
(Continued)

(56) References Cited

U.S. PATENT DOCUMENTS

| 5,650,054 A | * | 7/1997 | Shen .................... G01N 33/004 204/412 |
| 6,165,347 A | | 12/2000 | Warburton |

(Continued)

FOREIGN PATENT DOCUMENTS

| CN | 103808900 A | 5/2014 |
| CN | 205246490 U | * 5/2016 |

(Continued)

OTHER PUBLICATIONS

Cheng et al. "Design and fabrication of piezoelectric actuated valve micropump and its application in electronic cooling",<http://aolea.itri.org.tw/files/columnist/20130503180526024310/file/1/B09-2.pdf>.

(Continued)

*Primary Examiner* — Marrit Eyassu
(74) *Attorney, Agent, or Firm* — Birch, Stewart, Kolasch & Birch, LLP

(57) ABSTRACT

A device includes a main body and at least one actuating and sensing module. A length of the main body is 5~40 mm. A width of the main body is 5~27 mm. A height of the main body is 2~10 mm. The actuating and sensing module is disposed in the main body. The actuating and sensing module includes a carrier, at least one sensor, at least one actuating device, a driving and transmitting controller and a battery. The sensor, the actuating device, the driving and transmitting controller and the battery are disposed on the carrier. The actuating device is disposed on one side of the sensor. The actuating device includes at least one guiding (Continued)

channel. The actuating device is enabled to transport fluid to flow toward the sensor through the guiding channel so as to make the fluid measured by the sensor.

18 Claims, 12 Drawing Sheets

(51) Int. Cl.
    *G01N 33/00* (2006.01)
    *F04B 53/20* (2006.01)
    *G01N 1/22* (2006.01)
    *H04L 67/10* (2022.01)
    *F04B 39/16* (2006.01)

(52) U.S. Cl.
    CPC .......... *G01N 33/0062* (2013.01); *F04B 39/16* (2013.01); *G01N 33/004* (2013.01); *G01N 33/0039* (2013.01); *G01N 33/0047* (2013.01); *H04L 67/10* (2013.01)

(58) Field of Classification Search
    CPC ........... G01N 33/0039; G01N 33/0047; G01N 33/004; H04L 67/10; Y02A 50/20
    USPC ......................................................... 73/31.02
    See application file for complete search history.

(56) References Cited

U.S. PATENT DOCUMENTS

| | | | | |
|---|---|---|---|---|
| 7,395,692 B2 * | 7/2008 | Wansing | ................ | G01N 27/16 422/94 |
| 2009/0309744 A1 | 12/2009 | Fu et al. | | |
| 2010/0063409 A1 * | 3/2010 | Hok | ........ | A61B 5/097 600/532 |
| 2013/0276517 A1 * | 10/2013 | Takano | ................... | G01M 3/18 73/40.5 R |
| 2014/0134053 A1 * | 5/2014 | Mayer | ................ | G01N 33/0009 422/83 |
| 2014/0178220 A1 * | 6/2014 | Fujisaki | ................ | F04B 45/047 417/413.2 |
| 2014/0294046 A1 * | 10/2014 | Le Neel | ................... | G01W 1/02 374/143 |
| 2014/0377099 A1 * | 12/2014 | Hsueh | ..................... | F04B 49/22 417/413.2 |
| 2015/0219608 A1 * | 8/2015 | Choi | ........................ | G06F 3/017 73/23.2 |
| 2016/0209382 A1 * | 7/2016 | Shalom | .............. | G01N 33/0009 |
| 2016/0327532 A1 * | 11/2016 | Bather | ................ | G01N 33/0009 |
| 2017/0336343 A1 * | 11/2017 | Bhat | .................. | G01N 27/4163 |
| 2017/0368239 A1 * | 12/2017 | Askem | ................ | A61M 1/0072 |

FOREIGN PATENT DOCUMENTS

| | | | |
|---|---|---|---|
| CN | 205538890 U | | 8/2016 |
| CN | 106370575 A | * | 2/2017 |
| CN | 206036594 U | | 3/2017 |
| CN | 206038594 U | * | 3/2017 |
| TW | 200951888 A | | 12/2009 |
| TW | M525446 U | | 7/2016 |
| TW | M538545 U | | 3/2017 |
| TW | M543870 U | | 6/2017 |
| TW | M544653 U | | 7/2017 |

OTHER PUBLICATIONS

Indian Office Action dated Sep. 4, 2020 far Application No. 201824029825 with an English translation.

* cited by examiner

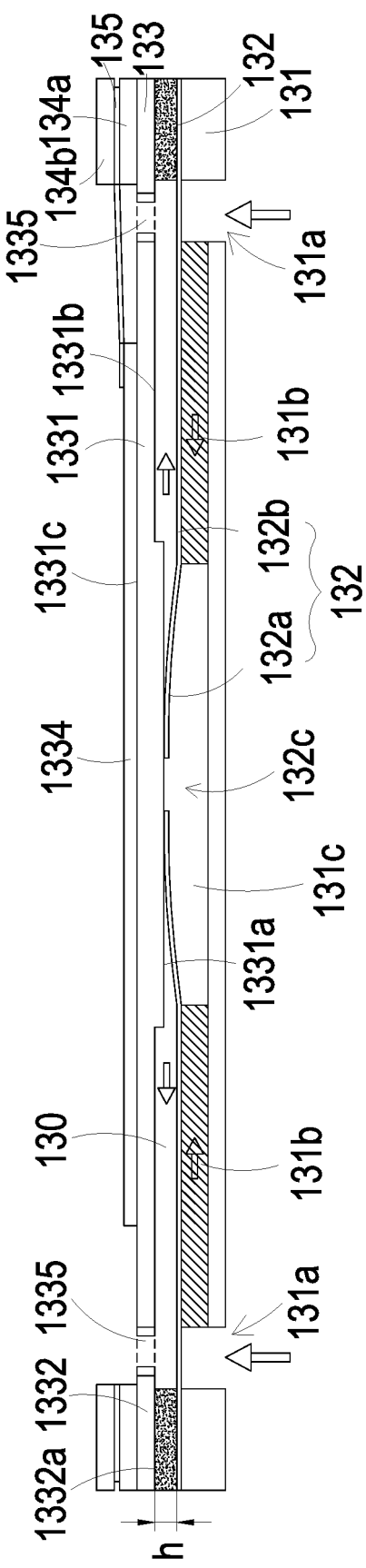
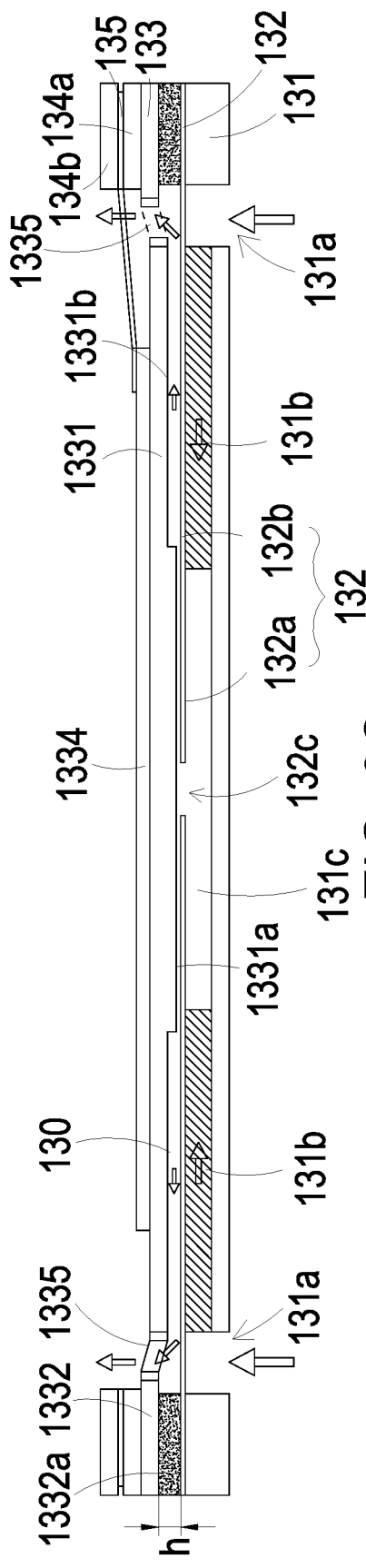
FIG. 6B
FIG. 6C

DEVICE HAVING ACTUATING AND SENSING MODULE

FIELD OF THE INVENTION

The present disclosure relates to an electronic device, and more particularly to a device having an actuating and sensing module applicable to an electronic device for monitoring environment.

BACKGROUND OF THE INVENTION

Nowadays, people pay much attention to air quality in the environment. For example, it is important to monitor carbon monoxide, carbon dioxide, volatile organic compounds (VOC), fine suspended particle (PM2.5), and so on. The exposure of these substances in the environment will cause human health problems or even harm the life. Therefore, it is important for every country to develop and implement the environmental monitoring technology.

As known, portable electronic devices are widely used and applied in the modern life. In other words, it is feasible to use the portable electronic device to monitor the ambient air. If the portable electronic device is capable of immediately providing people with the monitored information relating to the environment for caution, it may help people escape or prevent from the injuries and influence on human health caused by the exposure of these substances in the environment. In other words, the portable electronic device is suitably used for monitoring the ambient air in the environment.

Although it is obviously beneficial to make the portable electronic device equipped with sensor for collecting environment data, however, when the sensor is integrated into the electronic device, the monitoring sensitivity and the precision of the sensor should be taken into consideration. For example, the sensor is in contact with the fluid circulating from the outside and transferred by naturally occurring convection in the surroundings. In other words, the sensor fails to fetch a consistent flow to maintain stably monitoring. Since it is difficult to trigger response action of the sensor by the circulating fluid transferred by convection, the response time of the sensor is long and becomes a great factor affecting real-time monitoring.

Therefore, there is a need of providing a technology of increasing the monitoring accuracy of the sensor and decreasing the response time of the sensor.

SUMMARY OF THE INVENTION

An object of the present disclosure provides a device having an actuating and sensing module. The device includes a main body and at least one actuating and sensing module. The at least one actuating and sensing module is disposed in the main body. The length of the main body is in a range between 5 mm and 40 mm, the width of the main body is in a range between 5 mm and 27 mm, and the height of the main body is in a range between 2 mm and 10 mm. The ratio of the width to the height is in a range between 0.5 and 13.5. Consequently, the device is portable.

Another object of the present disclosure provides a device having an actuating and sensing module. The device includes a main body and at least one actuating and sensing module. The at least one actuating and sensing module is disposed in the main body. The actuating and sensing module includes a carrier, at least one sensor, at least one actuating device, a driving and transmitting controller and a battery, which are integrated as a modularized structure. The actuating device is used to increase the flow rate of fluid and provide the amount of fluid stably and uniformly. Since the sensor is provided with a stable and uniform amount of the fluid continuously, the time for enabling the sensor to monitor the fluid is largely reduced, thereby achieving the monitoring of the fluid more precisely.

A further object of the present disclosure provides a device having an actuating and sensing module. The device combining with the actuating and sensing module is used for monitoring the environment, thereby providing a portable device capable of monitoring the air quality. In other words, the device could monitor the air quality in the environment and transmit an output data of the monitored data to a connection device. The information carried in the output data may be displayed, stored and transmitted by the connection device. Consequently, the real-time information may be displayed and a real-time notification may be formed. Moreover, the output data could be uploaded for constructing a cloud database to enable an air quality notification mechanism and an air quality processing mechanism. Therefore, the people may take precautions against the air pollution immediately to prevent from the ill influence on human health caused by the air pollution.

In accordance with an aspect of the present disclosure, a device having actuating and sensing module is provided. The device includes a main body and at least one actuating and sensing module. A length of the main body is in a range between 5 mm and 40 mm. A width of the main body is in a range between 5 mm and 27 mm. A height of the main body is in a range between 2 mm and 10 mm. The at least one actuating and sensing module is disposed in the main body. The actuating and sensing module includes a carrier, at least one sensor, at least one actuating device, a driving and transmitting controller and a battery. The at least one sensor, the at least one actuating device, the driving and transmitting controller and the battery are disposed on the carrier. The at least one actuating device is disposed on one side of the at least one sensor and includes at least one guiding channel. The actuating device is enabled to transport fluid to flow toward the sensor through the guiding channel so as to make the fluid measured by the sensor.

The above contents of the present disclosure will become more readily apparent to those ordinarily skilled in the art after reviewing the following detailed description and accompanying drawings, in which:

BRIEF DESCRIPTION OF THE DRAWINGS

FIGS. 6A to 6E schematically illustrate the actions of the fluid actuating device of the actuating and sensing module according to the embodiment of the present disclosure.

DETAILED DESCRIPTION OF THE PREFERRED EMBODIMENT

Figure 1A:
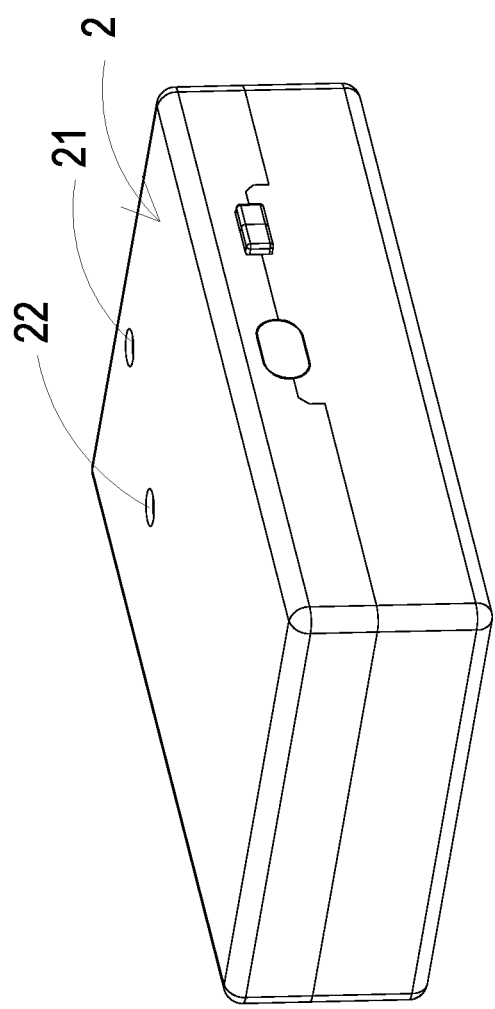
FIG. 1A is a schematic perspective view illustrating the outer appearance of a device having an actuating and sensing module according to an embodiment of the present disclosure.
Figure 1C:
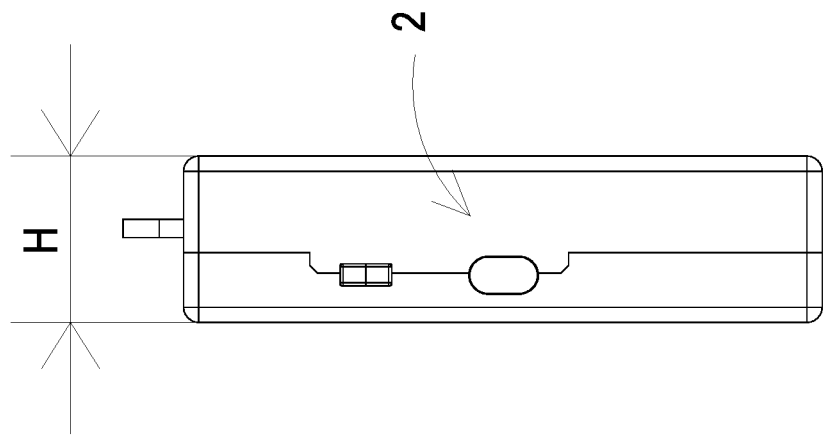
FIG. 1C is a schematic side view illustrating the device having the actuating and sensing module of FIG. 1A.
Figure 1B:
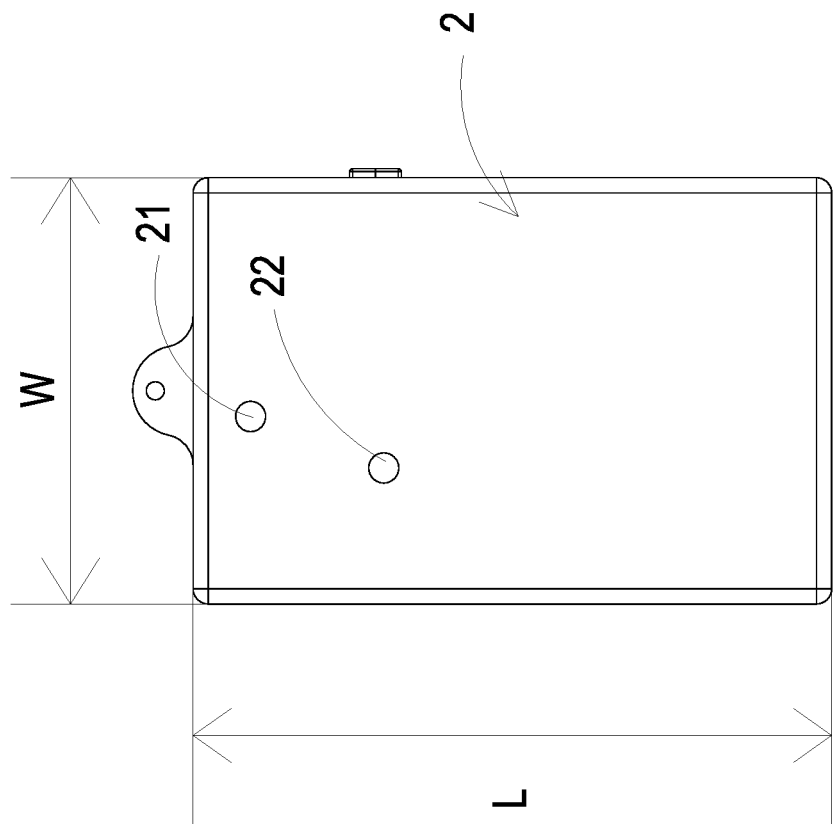
FIG. 1B is a schematic front view illustrating the device having the actuating and sensing module of FIG. 1A.

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Please refer to FIGS. 1A, 1B, 1C, 2A, 2B and 2C. The present disclosure provides a device having an actuating and sensing module including at least one main body 2, at least one length L, at least one width W, at least one height H, at least one actuating and sensing module 1, at least one carrier 11, at least one sensor 12, at least one actuating device 13, at least one driving and transmitting controller 14, at least one battery 15, at least one guiding channel 136 and at least one fluid. The number of the main body 2, the length L, the width W, the height H, the carrier 11, the driving and transmitting controller 14, the battery 15 and the fluid is exemplified by one for each in the following embodiments but not limited thereto. It is noted that each of the main body 2, the length L, the width W, the height H, the carrier 11, the driving and transmitting controller 14, the battery 15 and the fluid can also be provided in plural numbers.

Please refer to FIGS. 1A, 1B, 1C, 2A, 2B and 2C. The device having the actuating and sensing module includes a main body 2 and at least one actuating and sensing module 1. The main body 2 has a length L, a width W and a height H. The actuating and sensing module 1 is disposed in the main body 2 and includes a carrier 11, at least one sensor 12, at least one actuating device 13, a driving and transmitting controller 14 and a battery 15. The main body 2 is a hollow casing with an inlet port 21 and an outlet port 22.

For achieving the portable purpose of the device having the actuating and sensing module, it is necessary to minimize the entire volume and weightiness of the main body 2. In order to miniaturize the main body 2 to achieve the portable purpose for the user, the sizes of the modules disposed within the main body 2 should be taken into consideration. Therefore, the components of the actuating and sensing module 1 also need to be miniaturized. Since the sensor 12, the driving and transmitting controller 14 and the battery 15 of the actuating and sensing module 1 are electronic components, the sizes of these electronic components can be miniaturized. However, the actuating device 13 is an actuating device, for achieving the actuating and vibrating purpose of the internal chamber, the actuating device 13 needs to have sufficient volume. In order to match with the size and volume of a current most miniaturized actuating device, the size of the main body 2 should be specially designed as follows so as to achieve miniaturization. In this embodiment, the length L of the main body 2 is in the range between 5 mm and 40 mm, the width W of the main body 2 is in the range between 5 mm and 27 mm, and the height H of the main body 2 is in the range between 2 mm and 10 mm. The ratio of the width W to the height H is in the range between 0.5 and 13.5. The main body 2 is miniaturized and thinned. Consequently, the device having the actuating and sensing module is portable.

Please refer to FIGS. 2A, 2B and 2C again. The carrier 11 of the actuating and sensing module 1 is a platform for integrating the sensor 12, the actuating device 13, the driving and transmitting controller 14 and the battery 15. In an embodiment, the carrier 11 is a substrate such as a printed circuit board (PCB). An array of the sensor 12 and the actuating device 13 is disposed on the carrier 11. It is noted that the example of the carrier 11 is not restricted, and the carrier 11 may be other platform for supporting and integrating the sensor 12 and the actuating device 13. In an embodiment, the actuating and sensing module 1 further includes a monitoring chamber 16. The sensor 12 and the actuating device 13 are disposed in the monitoring chamber 16. The monitoring chamber 16 includes an inlet passage 161 and an outlet passage 162. When the actuating and sensing module 1 is disposed in the main body 2, the inlet passage 161 is aligned with the inlet port 21 of the main body 2 and the outlet passage 162 is aligned with the outlet port 22 of the main body 2. The inlet passage 161 and the outlet passage 162 are covered by two protective films 17, respectively. That is, the two protective films 17 are aligned with the inlet port 21 and the outlet port 22 of the main body 2, respectively. In an embodiment, the protective films 17 are waterproof and dustproof film structures, and only the gas is permitted to pass through the protective films 17. Consequently, the fluid (that is, the gas in this embodiment) inputted into the inlet passage 161 and outputted from the outlet passage 162 will be filtered by the protective films 17 in a waterproof and dustproof manner.

In this embodiment, the sensor 12 is located under the inlet passage 161. The actuating device 13 is aligned with the outlet passage 162. Moreover, the actuating device 13 is disposed on one side of the sensor 12 and includes at least one guiding channel 136. The actuating device 13 is enabled to transport the fluid to flow in the direction indicated by the arrows (see FIG. 2C). Consequently, the guiding channel 136 inhales the fluid for allowing the fluid introduced from the inlet passage 161 to flow to the sensor 12 and measured by the sensor 12. Since the fluid is guided to the sensor 12 by the actuating device 13 and the sensor 12 is provided with a stable and uniform amount of the fluid continuously, the time for enabling the sensor 12 to monitor the fluid is largely reduced, thereby achieving the monitoring of the fluid more precisely.

An example of the sensor 12 includes but is not limited to a temperature sensor, a volatile organic compound sensor (e.g., a sensor for measuring formaldehyde or ammonia gas), a particulate sensor (e.g., a fine suspended particle (PM2.5) sensor), a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, or the combination thereof. Alternatively, the sensor 12 is a bacterial sensor, a virus sensor, a microorganism sensor, or the combination thereof.

The actuating device 13 is a driving device capable of driving a desired system in response to a control signal. An example of the actuating device 13 includes but is not limited to an electric actuating device, a magnetic actuating device, a thermal actuating device, a piezoelectric actuating device, a fluid actuating device, or the combination thereof. For example, the electric actuating device is a DC motor, an AC motor or a step motor, the magnetic actuating device is a magnetic coil motor, the thermal actuating device is a heat pump, the piezoelectric actuating device is a piezoelectric pump, and the fluid actuating device is a gas pump or a liquid pump.

In an embodiment, the actuating device 13 of the actuating and sensing module 1 is a fluid actuating device. In the embodiment, the actuating device 13 may be a driving structure of a piezoelectric actuating pump or a driving structure of a micro-electro-mechanical system (MEMS) pump. Hereinafter, the actions of the fluid actuating device 13 of a piezoelectric pump will be described as follows.

Figure 3A:
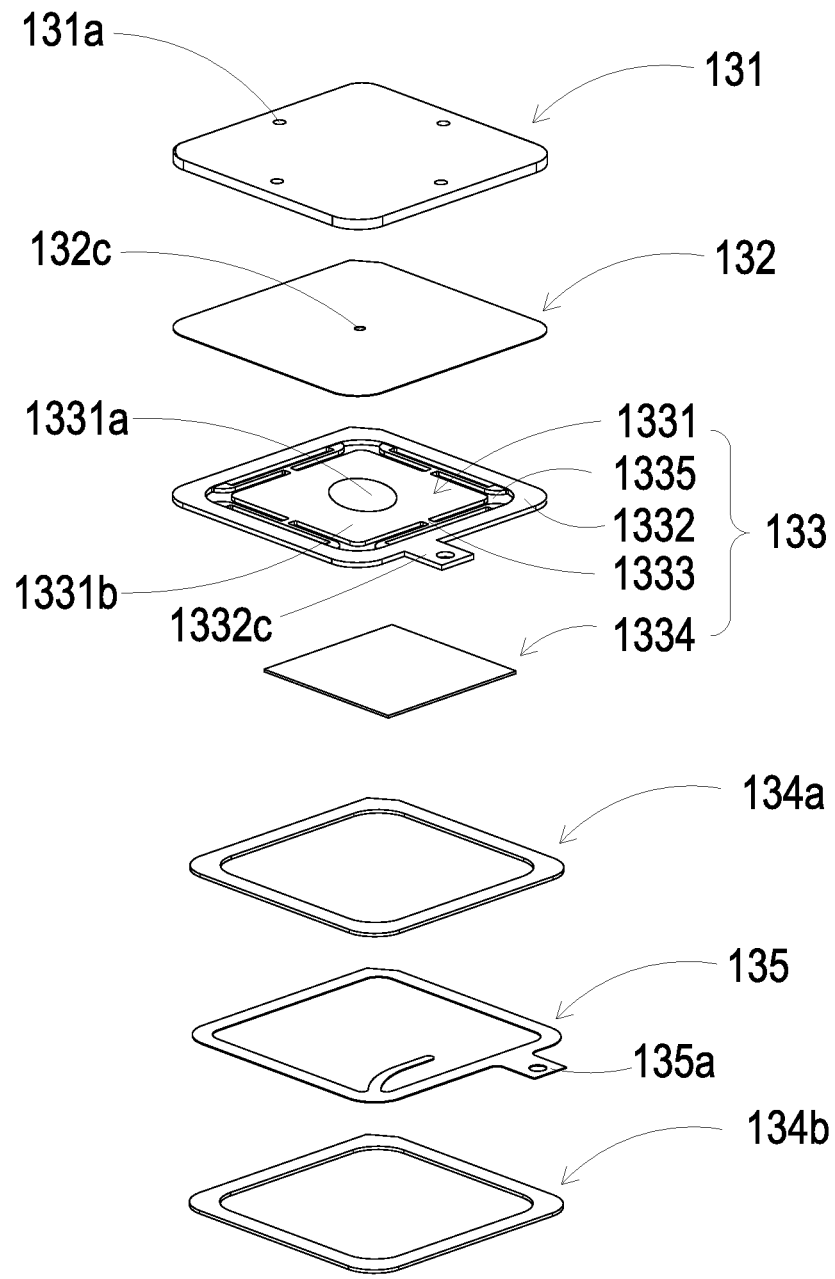
FIG. 3A is a schematic exploded view illustrating a fluid actuating device used in the actuating and sensing module of the device according to the embodiment of the present disclosure.
Figure 3B:
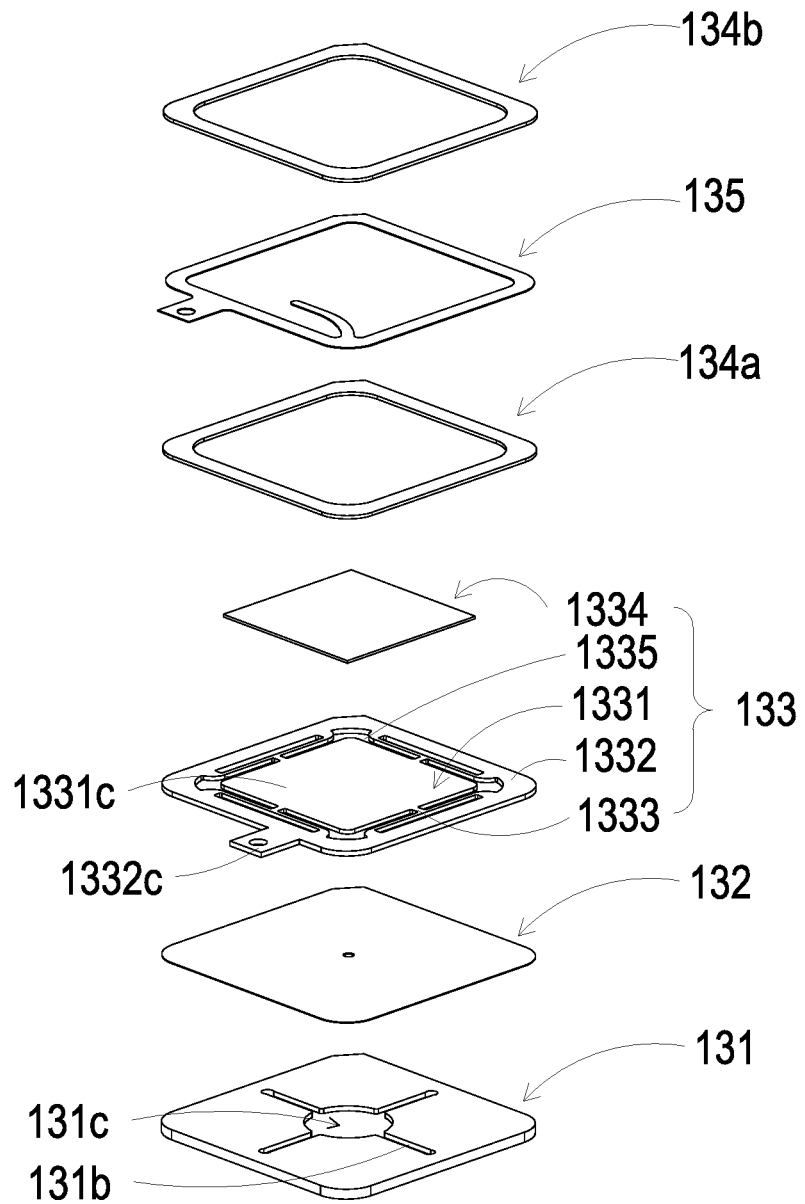
FIG. 3B is a schematic exploded view illustrating the fluid actuating device of FIG. 3A and taken along another viewpoint.
Figure 5:
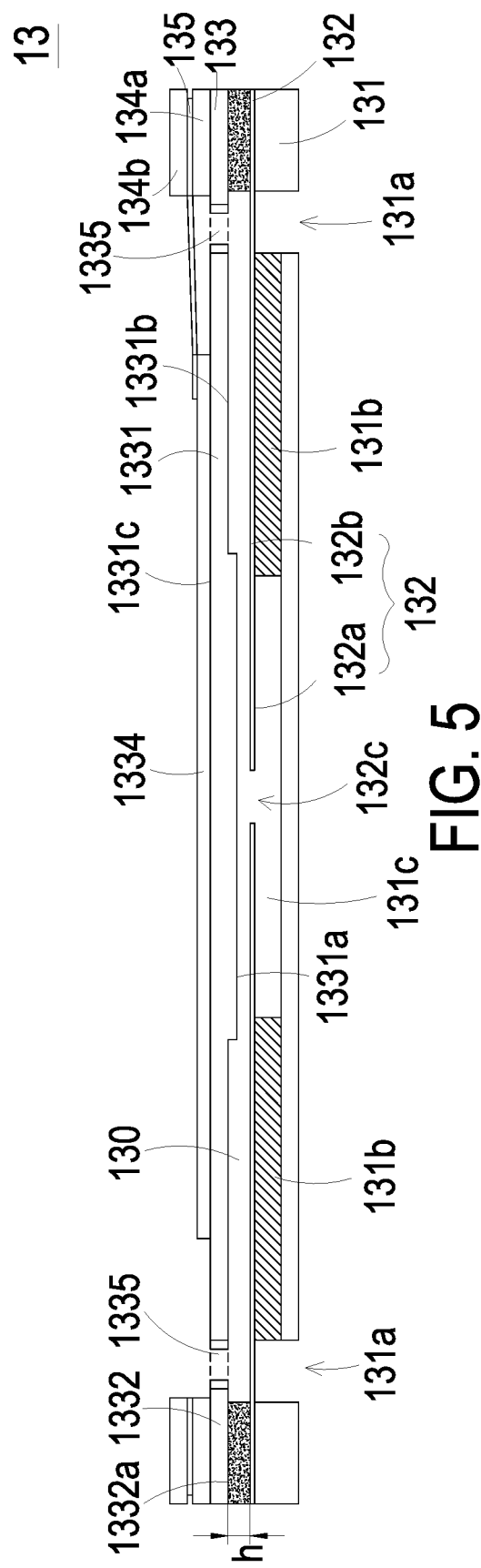
FIG. 5 is a schematic cross-sectional view illustrating the fluid actuating device of the actuating and sensing module as shown in FIGS. 3A and 3B.

Please refer to FIGS. 3A and 3B. The actuating device 13 includes a fluid inlet plate 131, a resonance plate 132, a piezoelectric actuator 133, a first insulation plate 134*a*, a conducting plate 135 and a second insulation plate 134*b*. The piezoelectric actuator 133 is aligned with the resonance plate 132. The fluid inlet plate 131, the resonance plate 132, the piezoelectric actuator 133, the first insulation plate 134*a*, the conducting plate 135 and the second insulation plate 134*b* are stacked on each other sequentially. After the above components are combined together, the cross-sectional view of the resulting structure of the actuating device 13 is shown in FIG. 5.

In the embodiment, the fluid inlet plate 131 has at least one inlet 131*a*. Preferably but not exclusively, the fluid inlet plate 131 has four inlets 131*a*. The inlets 131*a* run through the fluid inlet plate 131. In response to the action of the atmospheric pressure, the fluid can be introduced into the actuating device 13 through the at least one inlet 131*a*. Moreover, at least one convergence channel 131*b* is formed on a first surface of the fluid inlet plate 131, and is in communication with the at least one inlet 131*a* on a second surface of the fluid inlet plate 131. Moreover, a central cavity 131*c* is located at the intersection of the convergence channels 131*b*. The central cavity 131*c* is in communication with the at least one convergence channel 131*b*, such that the fluid from the at least one inlet 131*a* would be introduced into the at least one convergence channel 131*b* and is guided to the central cavity 131*c*. Consequently, the fluid can be transferred by the actuating device 13. In this embodiment, the at least one inlet 131*a*, the at least one convergence channel 131*b* and the central cavity 131*c* of the fluid inlet plate 131 are integrally formed from a single structure. The central cavity 131*c* forms a convergence chamber for temporarily storing the fluid. In some embodiments, the fluid inlet plate 131 may be, for example, made of stainless steel. Moreover, the depth of the convergence chamber defined by the central cavity 131*c* is equal to the depth of the at least one convergence channel 131*b*. The resonance plate 132 may be made of, but not limited to a flexible material. The resonance plate 132 has a central aperture 132*c* corresponding to the central cavity 131*c* of the fluid inlet plate 131, so as to allow the fluid to flow therethrough. In other embodiments, the resonance plate 132 may be, for example, made of copper, but not limited thereto.

The piezoelectric actuator 133 includes a suspension plate 1331, an outer frame 1332, at least one bracket 1333 and a piezoelectric plate 1334. The piezoelectric plate 1334 is attached on a first surface 1331*c* of the suspension plate 1331. In response to an applied voltage, the piezoelectric plate 1334 would be subjected to a deformation. When the piezoelectric plate 1334 is subjected to the deformation, it facilitates a bending vibration of the suspension plate 1331. In this embodiment, the at least one bracket 1333 is connected between the suspension plate 1331 and the outer frame 1332, while the two ends of the bracket 1333 are connected with the outer frame 1332 and the suspension plate 1331 respectively such that the bracket 1333 can elastically support the suspension plate 1331. At least one vacant space 1335 is formed among the bracket 1333, the suspension plate 1331 and the outer frame 1332. The at least one vacant space 1335 is in communication with a guiding channel for allowing the fluid to go through. The type of the suspension plate 1331 and the outer frame 1332 and the type and the number of the at least one bracket 1333 may be varied according to the practical requirements. The outer frame 1332 is arranged around the suspension plate 1331. Moreover, a conducting pin 1332*c* is protruded outwardly from the outer frame 1332 so as to provide the function of electrical connection, but the present disclosure is not limited thereto.

Figure 4:
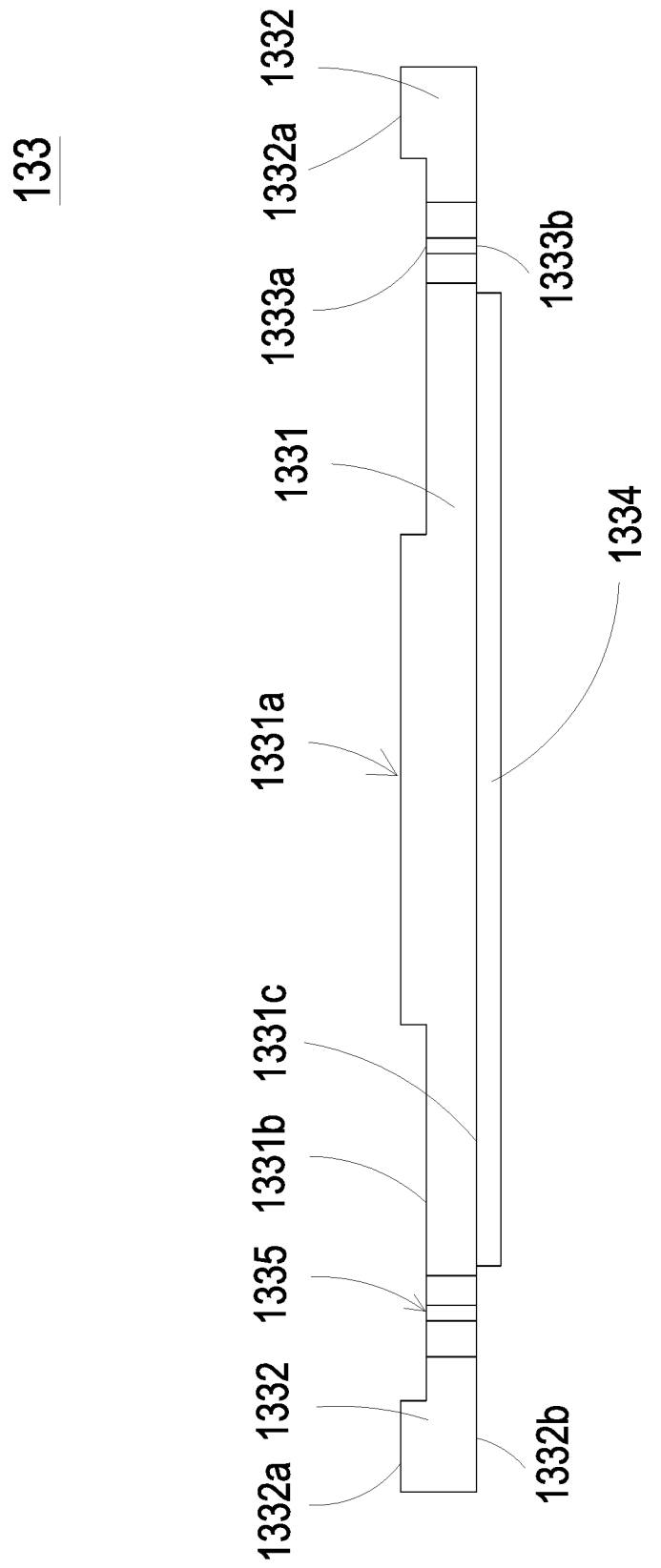
FIG. 4 is a schematic cross-sectional view illustrating the piezoelectric actuator of the fluid actuating device as shown in FIGS. 3A and 3B.

As shown in FIG. 4, the suspension plate 1331 has a bulge 1331*a* that makes the suspension plate 1331 a stepped structure. The bulge 1331*a* is formed on a second surface 1331*b* of the suspension plate 1331. The bulge 1331*a* may be for example but not limited to a circular convex structure. A top surface of the bulge 1331*a* of the suspension plate 1331 is coplanar with a second surface 1332*a* of the outer frame 1332, while the second surface 1331*b* of the suspension plate 1331 is coplanar with a second surface 1333*a* of the bracket 1333. Moreover, there is a specific depth from the bulge 1331*a* of the suspension plate 1331 (or the second surface 1332*a* of the outer frame 1332) to the second surface 1331*b* of the suspension plate 1331 (or the second surface 1333*a* of the bracket 1333). A first surface 1331*c* of the suspension plate 1331, a first surface 1332*b* of the outer frame 1332 and a first surface 1333*b* of the bracket 1333 are coplanar with each other. The piezoelectric plate 1334 is attached on the first surface 1331*c* of the suspension plate 1331. In some other embodiments, the suspension plate 1331 may be a square plate structure with two flat surfaces, but the type of the suspension plate 1331 may be varied according to the practical requirements. In this embodiment, the suspension plate 1331, the at least bracket 1333 and the outer frame 1332 may be integrally formed from a metal plate, which may be for example but not limited to a stainless steel material. In an embodiment, the length of a side of the piezoelectric plate 1334 is smaller than the length of a side of the suspension plate 1331. In another embodiment, the length of a side of the piezoelectric plate 1334 is equal to the length of a side of the suspension plate 1331. Similarly, the piezoelectric plate 1334 is a square plate structure corresponding to the suspension plate 1331 in terms of the design.

In this embodiment, the first insulation plate 134*a*, the conducting plate 135 and the second insulation plate 134*b* of the actuating device 13 are stacked on each other sequentially and located under the piezoelectric actuator 133, as shown in FIG. 3A. The profiles of the first insulation plate 134a, the conducting plate 135 and the second insulation plate 134b substantially match the profile of the outer frame 1332 of the piezoelectric actuator 133. In some embodiments, the first insulation plate 134a and the second insulation plate 134b may be made of an insulating material, for example but not limited to a plastic material, so as to provide insulating efficacy. In other embodiments, the conducting plate 135 may be made of an electrically conductive material, for example but not limited to a metallic material, so as to provide electrically conducting efficacy. In this embodiment, the conducting plate 135 may have a conducting pin 135a disposed thereon so as to provide the function of electrical connection.

Please refer to FIG. 5. In an embodiment, the fluid inlet plate 131, the resonance plate 132, the piezoelectric actuator 133, the first insulation plate 134a, the conducting plate 135 and the second insulation plate 134b of the actuating device 13 are stacked on each other sequentially. Moreover, there is a gap h between the resonance plate 132 and the outer frame 1332 of the piezoelectric actuator 133. In this embodiment, the gap h between the resonance plate 132 and the outer frame 1332 of the piezoelectric actuator 133 may be filled with a filler, for example but not limited to a conductive adhesive, so that a depth from the resonance plate 132 to the bulge 1331a of the suspension plate 1331 of the piezoelectric actuator 133 can be maintained. The gap h ensures the proper distance between the resonance plate 132 and the bulge 1331a of the suspension plate 1331 of the piezoelectric actuator 133, so that the fluid can be transferred quickly, the contact interference is reduced and the generated noise is largely reduced. In some embodiments, alternatively, the height of the outer frame 1332 of the piezoelectric actuator 133 is increased, so that the gap is formed between the resonance plate 132 and the piezoelectric actuator 133, but the present disclosure is not limited thereto.

Please refer to FIG. 3A, FIG. 3B and FIG. 5. After the fluid inlet plate 131, the resonance plate 132 and the piezoelectric actuator 133 are combined together, a movable part 132a and a fixed part 132b of the resonance plate 132 are defined. A convergence chamber for converging the fluid is defined by the movable part 132a of the resonance plate 132 and the fluid inlet plate 131 collaboratively. Moreover, a first chamber 130 is formed between the resonance plate 132 and the piezoelectric actuator 133 for temporarily storing the fluid. Through the central aperture 132c of the resonance plate 132, the first chamber 130 is in communication with the central cavity 131c of the fluid inlet plate 131. The peripheral regions of the first chamber 130 are in communication with the guiding channel through the vacant space 1335 between the brackets 1333 of the piezoelectric actuator 133.

Figure 6A:
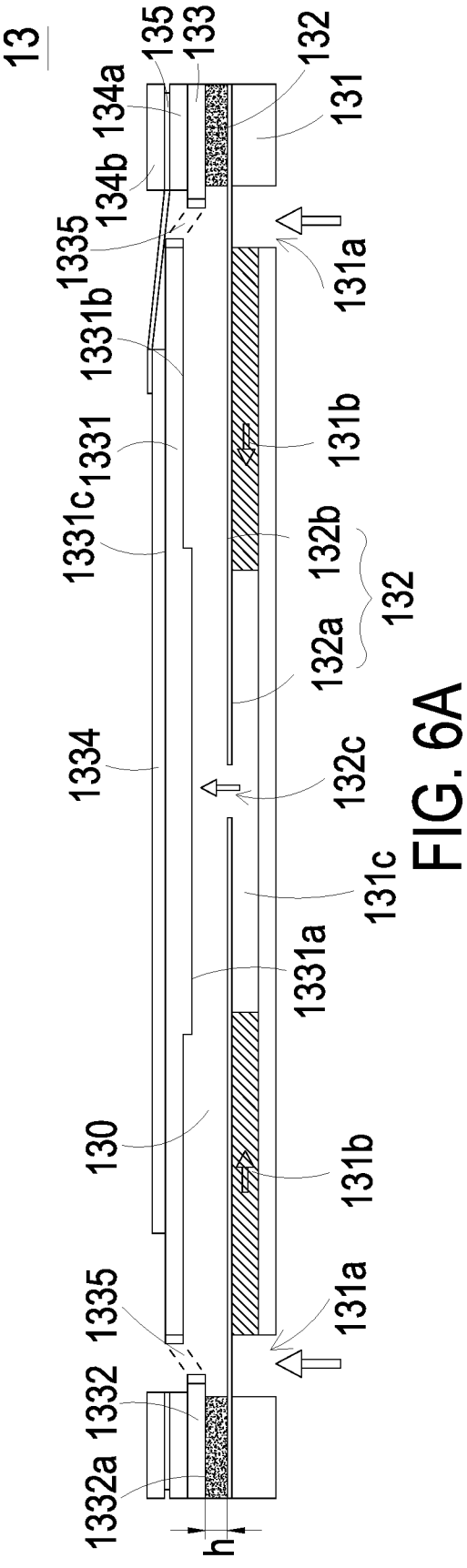
Figure 6D:
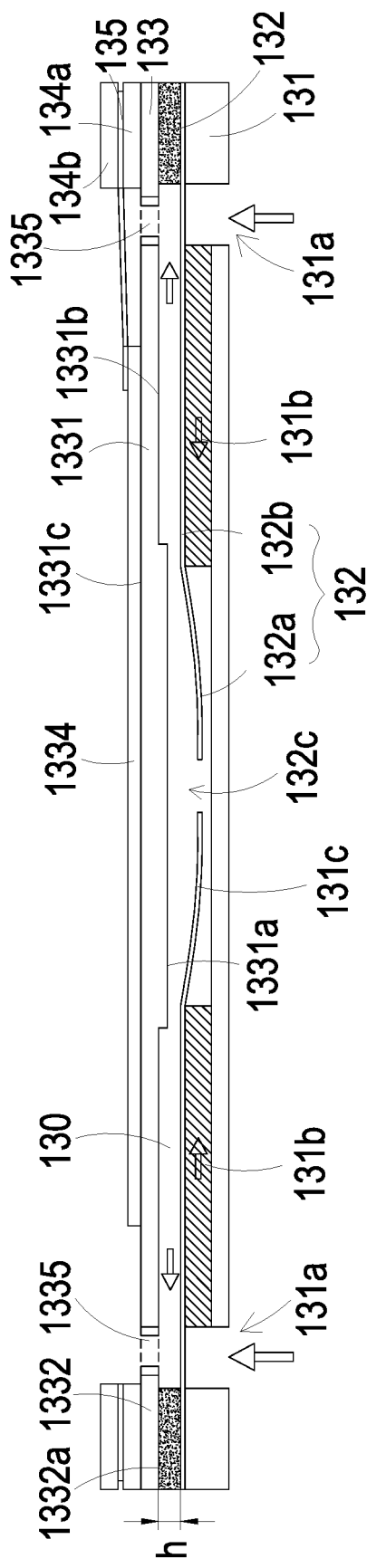
Figure 6E:
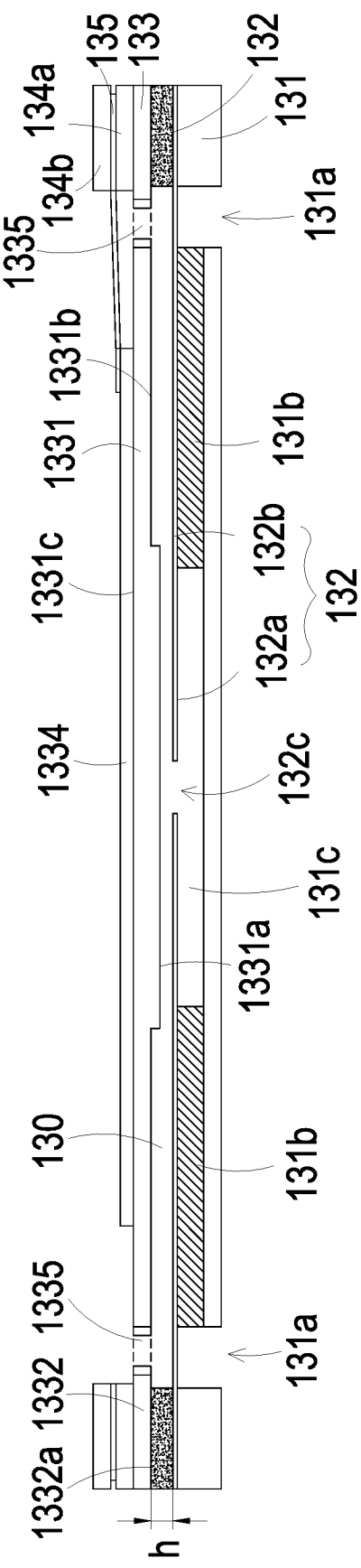

Please refer to FIG. 3A, FIG. 3B, FIG. 5 and FIGS. 6A to 6E. The actions of the actuating device 13 will be described as follows. When the actuating device 13 is enabled, the piezoelectric actuator 133 vibrates along a vertical direction in a reciprocating manner by using the bracket 1333 as a fulcrum. Please refer to FIG. 6A, the piezoelectric actuator 133 vibrates along first direction in response to the applied voltage. Since the resonance plate 132 is light and thin, the resonance plate 132 vibrates along the vertical direction in the reciprocating manner in resonance with the piezoelectric actuator 133. More especially, a region of the resonance plate 132 spatially corresponding to the central cavity 131c of the fluid inlet plate 131 is also subjected to a bending deformation. The region of the resonance plate 132 corresponding to the central cavity 131c of the fluid inlet plate 131 is the movable part 132a of the resonance plate 132. When the piezoelectric actuator 133 vibrates along first direction, the movable part 132a of the resonance plate 132 is subjected to the bending deformation because the movable part 132a of the resonance plate 132 is pushed by the fluid and vibrates in response to the piezoelectric actuator 133. In response to the vibration of the piezoelectric actuator 133 along first direction, the fluid is fed into the at least one inlet 131a of the fluid inlet plate 131. Then, the fluid is transferred to the central cavity 131c of the fluid inlet plate 131 through the at least one convergence channel 131b. Then, the fluid is transferred through the central aperture 132c of the resonance plate 132 spatially corresponding to the central cavity 131c, and introduced into the first chamber 130 along first direction. As the piezoelectric actuator 133 is enabled, the resonance of the resonance plate 132 occurs. Consequently, the resonance plate 132 vibrates along the vertical direction in the reciprocating manner. As shown in FIG. 6B, during the vibration of the movable part 132a of the resonance plate 132 at this stage, the movable part 132a of the resonance plate 132 moves along first direction to contact and attach on the bulge 1331a of the suspension plate 1331 of the piezoelectric actuator 133, and a distance from the fixed part 132b of the resonance plate 132 to a region of the suspension plate 1331 except the bulge 1331a remains the same. Owing to the deformation of the resonance plate 132 described above, a middle communication space of the first chamber 130 is closed, and the volume of the first chamber 130 is compressed. Under this circumstance, the pressure gradient occurs to push the fluid in the first chamber 130 moving toward peripheral regions of the first chamber 130 and flowing along first direction through the vacant space 1335 of the piezoelectric actuator 133. Referring to FIG. 6C, the movable part 132a of the resonance plate 132 has returned to its original position when the piezoelectric actuator 133 vibrates along second direction. Consequently, the volume of the first chamber 130 is continuously compressed to generate the pressure gradient which makes the fluid in the first chamber 130 continuously pushed toward peripheral regions. Meanwhile, the fluid is continuously fed into the at least one inlet 131a of the fluid inlet plate 131, and transferred to the central cavity 131c. Then, as shown in FIG. 6D, the resonance plate 132 moves along second direction, which is cause by the resonance of the piezoelectric actuator 133. That is, the movable part 132a of the resonance plate 132 is also vibrated along second direction. Consequently, it decreases the flow of the fluid from the at least one inlet 131a of the fluid inlet plate 131 into the central cavity 131c. At last, as shown in FIG. 6E, the movable part 132a of the resonance plate 132 has returned to its original position. As the embodiments described above, when the resonance plate 132 vibrates along the vertical direction in the reciprocating manner, the gap h between the resonance plate 132 and the piezoelectric actuator 133 is helpful to increase the maximum displacement along the vertical direction during the vibration. In other words, the configuration of the gap h between the resonance plate 132 and the piezoelectric actuator 133 can increase the amplitude of vibration of the resonance plate 132. Consequently, a pressure gradient is generated in the guiding channels of the actuating device 13 to facilitate the fluid to flow at a high speed. Moreover, since there is an impedance difference between the feeding direction and the exiting direction, the fluid can be transmitted from the inlet side to the outlet side. Even if a gas pressure exists at the outlet side, the actuating device 13 still has the capability of pushing the fluid to the guiding channel while achieving the silent efficacy. The steps of FIGS. 6A to 6E may be done repeatedly. Consequently, the ambient fluid is transferred from the outside to the inside by the actuating device 13.

Figure 2A:
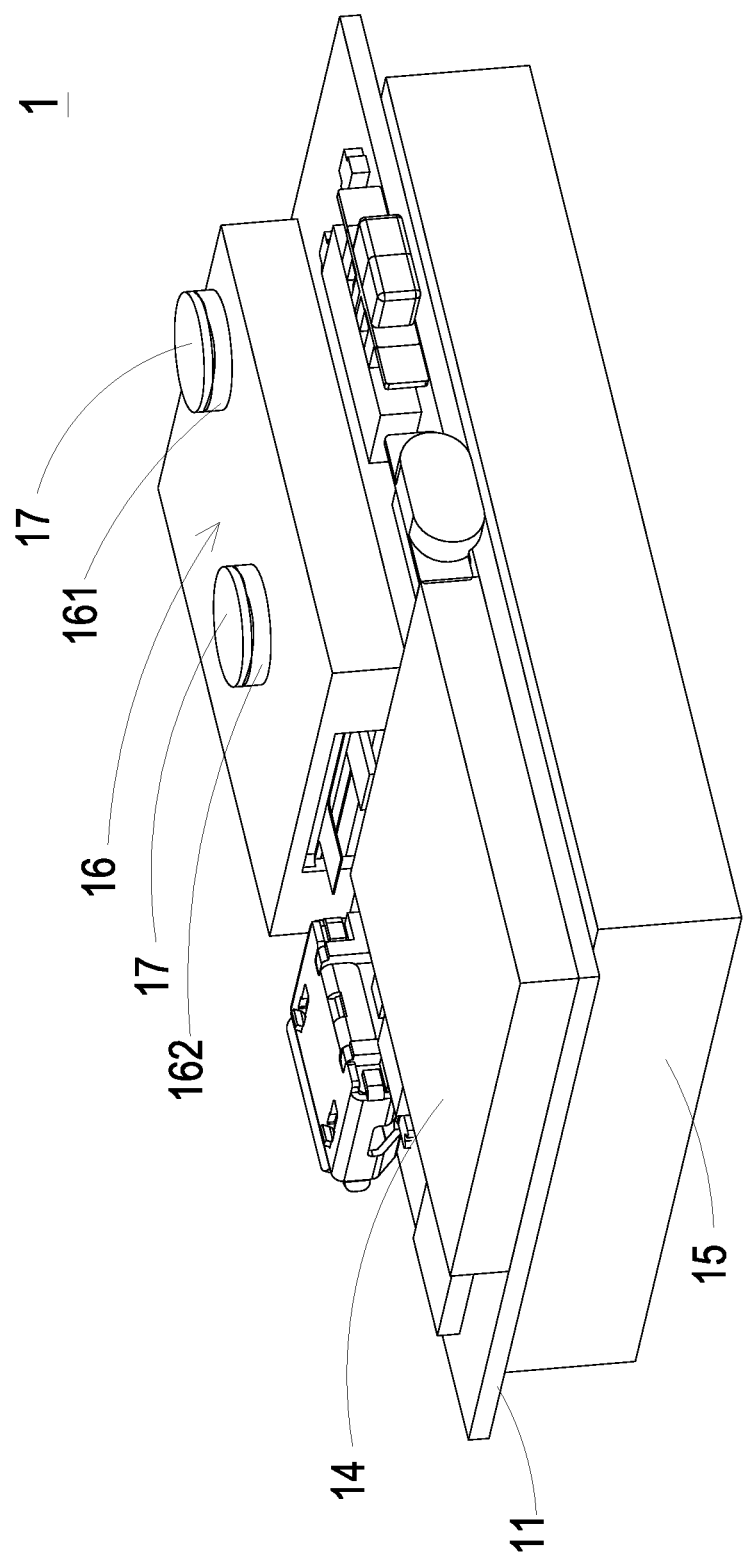
FIG. 2A is a schematic perspective view illustrating the actuating and sensing module of the device according to the embodiment of the present disclosure, in which a monitoring chamber is disposed on the carrier.
Figure 2B:
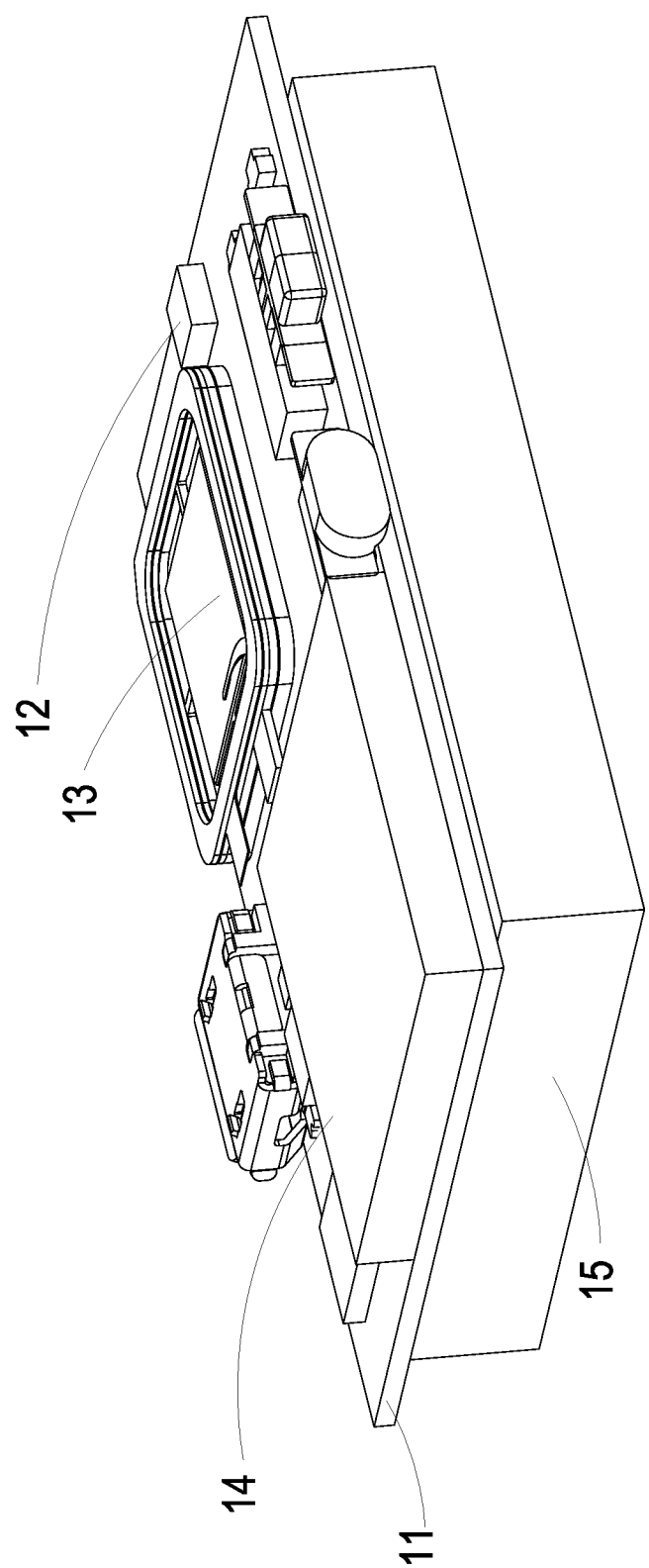
FIG. 2B is a schematic view illustrating the actuating and sensing module of FIG. 2A, in which an actuating device and a senor are disposed in the monitoring chamber.
Figure 2C:
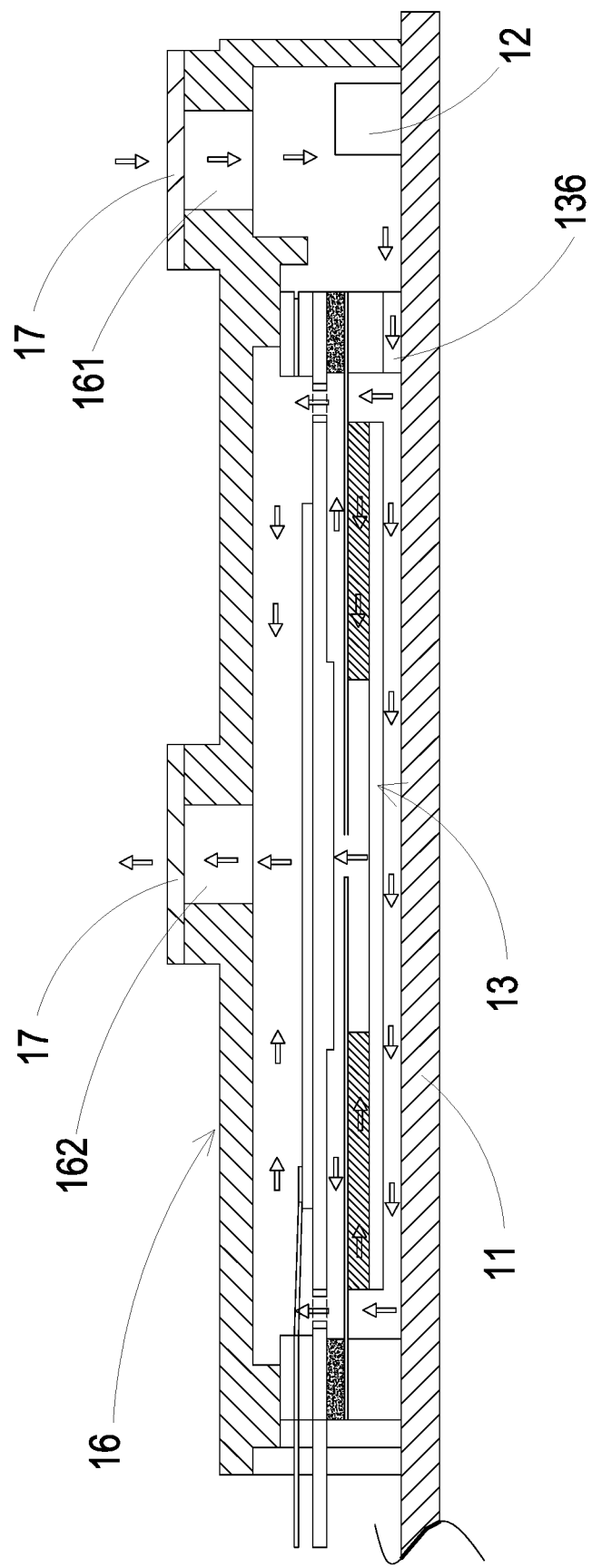
FIG. 2C is a schematic cross-sectional view illustrating the actuating and sensing module of FIG. 2B and the path of the fluid that is guided by the actuating and sensing module of the device according to the embodiment of the present disclosure.

As mentioned above, the actions of the actuating device 13 is further described as below. The fluid inlet plate 131, the resonance plate 132, the piezoelectric actuator 133, the first insulation plate 134a, the conducting plate 135 and the second insulation plate 134b are stacked on each other sequentially. As shown in FIG. 2C, the actuating device 13 is disposed on the carrier 11, the guiding channel 136 is arranged between the actuating device 13 and the carrier 11. The guiding channel 136 is disposed on one side of the sensor 12. When the actuating device 13 is enabled, the fluid flows in the direction indicated by the arrows (see FIG. 2C). Consequently, the guiding channel 136 inhales the fluid for allowing the fluid introduced from the inlet passage 161 to flow to the sensor 12 and measured by the sensor 12. Since the fluid is guided to the sensor 12 by the actuating device 13 and the sensor 12 is provided with a stable and uniform amount of the fluid continuously, the time for enabling the sensor 12 to monitor the fluid is largely reduced, thereby achieving the monitoring of the fluid more precisely.

Figure 7:
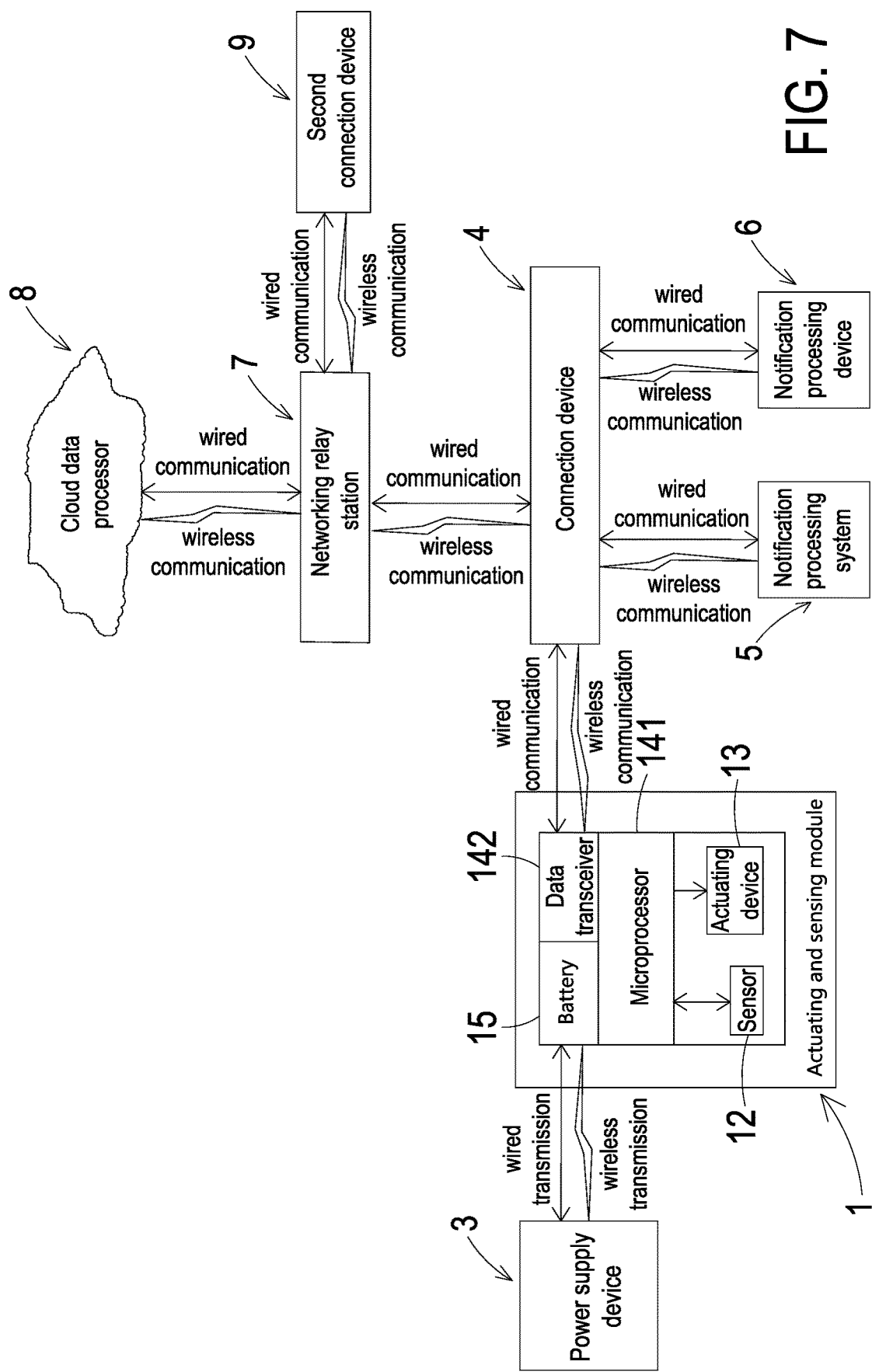
FIG. 7 schematically illustrates the architecture of a driving and information transmitting system according to an embodiment of the present disclosure.

FIG. 7 schematically illustrates the architecture of a driving and information transmitting system according to an embodiment of the present disclosure. The battery 15 of the actuating and sensing module 1 is used to store energy and output energy. The battery 15 transfers the energy to the sensor 12 and the actuating device 13 for powering the sensor 12 to perform a sensing operation and powering the actuating device 13 to perform an actuating operation under control. In an embodiment, the battery 15 is externally connected to a power supply device 3 to receive the energy from the power supply device 3, thereby enabling the sensor 12 and the actuating device 13. In an embodiment, the power supply device 3 may transfer the energy to the battery 15 through a wireless transmission path. For example, the power supply device 3 is a charger with a wireless charging component (or an inductive charging component), and the power supply device 3 transfers the energy to the battery 15 through a wireless transmission path. For example, the power supply device 3 is a chargeable battery with a wireless charging component (or an inductive charging component), and thus the power supply device 3 may transfer the energy to the battery 15 through the wireless transmission path. In another embodiment, the power supply device 3 is a portable electronic device with wireless charging/discharging function (e.g., a mobile phone with a wireless charging component (or an inductive charging component)), and thus the power supply device 3 may transfer the energy to the battery 15 through the wireless transmission path.

The driving and transmitting controller 14 of the actuating and sensing module 1 includes a microprocessor 141 and a data transceiver 142. The microprocessor 141 processes and calculates the measured data transmitted from the sensor 12 and controls the actuating of the actuating device 13. The data transceiver 142 may receive or transmit data. The microprocessor 141 processes and calculates the measured data transmitted from the sensor 12 to convert the measured data into an output data. The data transceiver 142 may receive the output data and transmit the output data to a connection device 4 through transmission. After that, the connection device 4 may display and store the information carried in the output data or transmit the information carried in the output data to a storage device to be stored and processed. In an embodiment, the connection device 4 is in communication with a notification processing system 5 to actively (e.g., directly notify) or passively (e.g., in response to the operation by a user who read the information carried in the output data) enable an air quality notification mechanism. For example, an instant air quality map informs people to avoid away or wear masks. In another embodiment, the connection device 4 is in communication with a notification processing device 6 to actively (e.g., directly notify) or passively (e.g., in response to the operation by a user who read the information carried in the output data) enable an air quality processing mechanism. For example, an air cleaner or an air-conditioner is enabled to clean the air.

In an embodiment, the connection device 4 is a display device with a wired communication module (e.g., a desktop computer). In another embodiment, the connection device 4 is a display device with a wireless communication module (e.g., a notebook computer). In another embodiment, the connection device 4 is a portable electronic device with a wireless communication module (e.g., a mobile phone). The wired communication module may have an RS485 communication port, an RS232 communication port, a Modbus communication port or a KNX communication port for wired communication. The wireless communication module may perform a wireless communication through a Zigbee communication technology, a Z-wave communication technology, an RF communication technology, a Bluetooth communication technology, a Wifi communication technology or an EnOcean communication technology.

The driving and information transmitting system further includes a networking relay station 7 and a cloud data processor 8. The connection device 4 is used to transmit the information carried in the output data to the networking relay station 7. Then, the information carried in the output data is transmitted from the networking relay station 7 to the cloud data processor 8 to be stored and processed. After the information carried in the output data is processed by the cloud data processor 8, the cloud data processor 8 issues a notification signal to the networking relay station 7. Then, the networking relay station 7 transmits the notification signal to the connection device 4. According to the notification signal, the notification processing system 5 connected with the connection device 4 enables an air quality notification mechanism. Alternatively, the notification processing device 6 connected with the connection device 4 enables an air quality processing mechanism.

In an embodiment, the connection device 4 issues a control command to the actuating and sensing module 1 so as to control the operation of the actuating and sensing module 1. Similarly, the control command may be transmitted to the data transceiver 142 through wired communication or wireless communication. Then, the control command is transmitted to the microprocessor 141 to control the sensor 12 to perform the sensing operation and enable the actuating device 13.

In an embodiment, the driving and information transmitting system further includes a second connection device 9 for issuing a control signal. After the second connection device 9 issues the control command to the cloud data processor 8 through the networking relay station 7, the control command is transmitted from the cloud data processor 8 to the connection device 4 through the networking relay station 7, so that the connection device 4 issues the control command to the data transceiver 142. Then, the control command is transmitted to the microprocessor 141. According to the control command, the microprocessor 141 controls the sensor 12 to perform the sensing operation and enables the actuating device 13. In an embodiment, the second connection device 9 is a device with a wired communication module. In another embodiment, the second connection device 9 is a device with a wireless communication module. In another embodiment, the second connection device 9 is a portable electronic device with a wireless communication module, but not limited thereto.

From the above descriptions, the present disclosure provides a device having an actuating and sensing module. The device combining with the actuating and sensing module is used to monitor the environment, thereby a portable device is provided to monitor the air quality. The actuating device is used to increase the flow rate of fluid and provide the amount of fluid stably and uniformly. Since the sensor is provided with a stable and uniform amount of the fluid continuously, the time for enabling the sensor to monitor the fluid is largely reduced, thereby achieving the monitoring of the fluid more precisely. Moreover, the actuating and sensing module may transmit an output data of the measured data to the connection device. The information carried in the output data may be displayed, stored and transmitted by the connection device. Consequently, the real-time information may be displayed and a real-time notification may be formed. Moreover, the output data could be uploaded for constructing a cloud database to enable an air quality notification mechanism and an air quality processing mechanism. Therefore, the people may take precautions against the air pollution immediately to prevent from the ill influence on human health caused by the air pollution. In other words, the device of the present disclosure is industrially valuable.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A device having actuating and sensing module, the device comprising:
    a main body having a length in a range between 5 mm and 40 mm, a width in a range between 5 mm and 27 mm and a height in a range between 2 mm and 10 mm; and
    at least one actuating and sensing module disposed in the main body, wherein the at least one actuating and sensing module comprises a carrier, at least one sensor, at least one actuating device, a driving and transmitting controller and a battery, wherein the at least one sensor, the at least one actuating device, the driving and transmitting controller and the battery are integrated with the carrier,
    wherein the actuating device is disposed on one side of the sensor and comprises at least one guiding channel and the at least one guiding channel is arranged between the at least one actuating device and the carrier, wherein the actuating device is enabled to transport fluid and the at least one guiding channel inhales the fluid for allowing the fluid to flow to the at least one sensor and measured by the at least one sensor,
    wherein the actuating and sensing module comprises a monitoring chamber, the sensor and the actuating device are disposed in the monitoring chamber, and the monitoring chamber comprises an inlet passage and an outlet passage, wherein the sensor is aligned with the inlet passage, and the actuating device is aligned with the outlet passage,
    wherein the main body comprises an inlet port and an outlet port, wherein the inlet passage is aligned with the inlet port of the main body, and the outlet passage is aligned with the outlet port of the main body.

2. The device according to claim 1, wherein a ratio of the width to the height is in a range between 0.5 and 13.5.

3. The device according to claim 1, wherein the inlet passage is covered by a first protective film, and the outlet passage is covered by a second protective film, wherein the first protective film is aligned with the inlet port of the main body, and the second protective film is aligned with the outlet port of the main body, thereby filtering the fluid and achieving waterproof and dustproof.

4. The device according to claim 1, wherein the sensor is at least one selected from the group consisting of a gas sensor, an oxygen sensor, a carbon monoxide sensor, a carbon dioxide sensor, a liquid sensor, a temperature sensor, a humidity sensor, an ozone sensor, a particulate sensor, a volatile organic compound sensor, a light sensor, a bacterial sensor, a virus sensor, a microorganism sensor, or the combination thereof.

5. The device according to claim 1, wherein the actuating device is a MEMS pump.

6. The device according to claim 1, wherein the actuating device is a piezoelectric pump.

7. The device according to claim 6, wherein the piezoelectric pump comprises:
    a fluid inlet plate having at least one inlet, at least one convergence channel and a central cavity defining a convergence chamber, wherein the at least one inlet allows the fluid to flow in, and the at least one convergence channel is disposed corresponding to the at least one inlet and guides the fluid from the at least one inlet toward the convergence chamber defined by the central cavity;
    a resonance plate having a central aperture and a movable part, wherein the central aperture is aligned with the convergence chamber and the movable part surrounds the central aperture; and
    a piezoelectric actuator aligned with the resonance plate, wherein a gap is formed between the resonance plate and the piezoelectric actuator to define a first chamber, so that the fluid from the at least one inlet of the fluid inlet plate is converged to the central cavity along the at least one convergence channel and flows into the first chamber through the central aperture of the resonance plate when the piezoelectric actuator is enabled, whereby the fluid is further transferred through a resonance between the piezoelectric actuator and the movable part of the resonance plate.

8. The device according to claim 7, wherein the piezoelectric actuator comprises:
    a suspension plate being a square suspension plate and having a first surface, an opposing second surface and a bulge, wherein the suspension plate is permitted to undergo a bending vibration;
    an outer frame arranged around the suspension plate;
    at least one bracket connected between the suspension plate and the outer frame for elastically supporting the suspension plate; and
    a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

9. The device according to claim 1, wherein the battery is adapted to store and output energy for powering the sensor to perform a sensing operation and powering the actuating device to perform an actuating operation, and the battery is capable of being externally connected to a power supply device to receive energy from the power supply device and store the energy.

10. The device according to claim 9, wherein the power supply device transfers the energy to the battery through a wired transmission path or a wireless transmission path, wherein the battery stores the energy and provides the energy to the sensor to perform a sensing operation and the actuating device to perform an actuating operation under control.

11. The device according to claim 1; wherein the driving and transmitting controller comprises:
- a microprocessor configured to process and calculate a measured data transmitted by the sensor and control the driving of the actuating device, wherein the measured data is processed into an output data by the microprocessor; and
- a data transceiver configured to receive and transmit data, wherein the data transceiver receives the output data and transmits the output data to a connection device, and the connection device displays, stores and transmits information carried in the output data.

12. The device according to claim 11, wherein the connection device is connected with a notification processing system or a notification processing device so as to enable an air quality notification mechanism or an air quality processing mechanism.

13. The device according to claim 11, wherein the connection device is a display device with a wired communication module, a display device with a wireless communication module or a portable electronic device with a wireless communication module.

14. The device according to claim 11, wherein the connection device transmits the information carried in the output data to a networking relay station, and the networking relay station transmits the information carried in the output data to a cloud data processor to be processed and stored.

15. The device according to claim 14, wherein after the information carried in the output data is processed by the cloud data processor, the cloud data processor issues a notification signal to the networking relay station and then transmits the notification signal to the connection device, wherein a notification processing system connected with the connection device is adapted to enable an air quality notification mechanism.

16. The device according to claim 14, wherein after the information carried in the output data is processed by the cloud data processor, the cloud data processor issues a notification signal to the networking relay station and then transmits the notification signal to the connection device, wherein a notification processing device connected with the connection device is adapted to enable an air quality processing mechanism.

17. The device according to claim 14, further comprising a second connection device to issue a control command, wherein after the second connection device issues the control command to the cloud data processor through the networking relay station, the control command is transmitted from the cloud data processor to the connection device through the networking relay station, so that the connection device issues the control command to the data transceiver.

18. A device having actuating and sensing module, the device comprising:
- at least one main body having at least one length in a range between 5 mm and 40 mm, at least one width in a range between 5 mm and 27 mm, and at least one height in a range between 2 mm and 10 mm; and
- at least one actuating and sensing module disposed in the at least one main body, wherein the at least one actuating and sensing module comprises at least one carrier, at least one sensor, at least one actuating device, at least one driving and transmitting controller and at least one battery, wherein the at least one sensor, the at least one actuating device, the at least one driving and transmitting controller and the at least one battery are integrated with the at least one carrier,
wherein the at least one actuating device is disposed on one side of the at least one sensor and comprises at least one guiding channel and the at least one guiding channel is arranged between the at least one actuating device and the carrier, wherein the at least one actuating device is enabled to transport at least one fluid and the at least one guiding channel inhales the at least one fluid for allowing the at least one fluid to flow to the at least one sensor and measured by the at least one sensor,
wherein the actuating and sensing module comprises a monitoring chamber, the sensor and the actuating device are disposed in the monitoring chamber, and the monitoring chamber comprises an inlet passage and an outlet passage, wherein the sensor is aligned with the inlet passage, and the actuating device is aligned with the outlet passage,
wherein the main body comprises an inlet port and an outlet port, wherein the inlet passage is aligned with the inlet port of the main body, and the outlet passage is aligned with the outlet port of the main body.

* * * * *